United States Patent
Holmes et al.

(10) Patent No.: US 6,903,557 B2
(45) Date of Patent: Jun. 7, 2005

(54) MICROWAVE MOISTURE SENSING VIA WAVEGUIDE WITH SLOT ARRAY

(75) Inventors: Wayne Stephen Holmes, Auckland (NZ); Stephen Geoffrey Riley, Rotorua (NZ)

(73) Assignees: New Zealand Forest Research Institute Limited, Rotorua (NZ); Industrial Research Institute Limited, Auckland (NZ)

(*) Notice: Subject to any disclaimer, the term of this patent is extended or adjusted under 35 U.S.C. 154(b) by 59 days.

(21) Appl. No.: 10/399,220

(22) PCT Filed: Oct. 11, 2001

(86) PCT No.: PCT/NZ01/00225

§ 371 (c)(1),
(2), (4) Date: Sep. 17, 2003

(87) PCT Pub. No.: WO02/31479

PCT Pub. Date: Apr. 18, 2002

(65) Prior Publication Data

US 2004/0124855 A1 Jul. 1, 2004

(30) Foreign Application Priority Data

Oct. 11, 2000 (NZ) .................................. 507469

(51) Int. Cl.$^7$ ......................... G01R 27/26; G01R 27/32
(52) U.S. Cl. ........................ 324/664; 324/638; 324/646
(58) Field of Search ................................. 324/664, 637, 324/638, 642, 643, 646

(56) References Cited

U.S. PATENT DOCUMENTS

| | | | |
|---|---|---|---|
| 5,103,181 A | * | 4/1992 | Gaisford et al. ............ 324/637 |
| 5,619,143 A | | 4/1997 | Stevens et al. ............. 324/639 |
| 6,411,106 B1 | | 6/2002 | Holmes et al. ............. 324/643 |

FOREIGN PATENT DOCUMENTS

| | | |
|---|---|---|
| WO | WO 90/09578 | 8/1990 |
| WO | WO 97/21992 | 6/1997 |

OTHER PUBLICATIONS

Derwent Abstract Accession No. 87–255693/36, SU 1285362 A (Zaporo Mech. Eng. Cons) Jan. 23, 1987 Abstract.

* cited by examiner

*Primary Examiner*—Jay Patidar
*Assistant Examiner*—Timothy J. Dole
(74) *Attorney, Agent, or Firm*—Sheldon & Mak

(57) ABSTRACT

A generator (6) directs microwave signals to a waveguide (1) having a linear array of slots (2), and the signals are received by measuring device (5). The local permittivity or moisture content of material adjacent the waveguide (1), such as a stack of timber, may be determined at each slot (2) via regression analysis. The total permittivity or moisture may be determined by averaging measurements obtained for both transmission directions of the waveguide (1). The apparatus may be used for controlling drying parameters, such as drying time, for the material.

24 Claims, 2 Drawing Sheets

MICROWAVE MOISTURE SENSING VIA WAVEGUIDE WITH SLOT ARRAY

CROSS-REFERENCE TO RELATED APPLICATIONS

This Application claims priority from International Application Number PCT/NZ01/00225, titled "Microwave Moisture Sensing Via Waveguide with Slot Array," filed Oct. 11, 2001, and New Zealand Application Number 507469, filed Oct. 11, 2000.

TECHNICAL FIELD

The present invention relates to an apparatus and method for sensing permittivity of a material, an in particular but not exclusively to moisture sensing using microwave technologies.

The invention particularly but not exclusively relates to the sensing of moisture in timber. However it will be appreciated by those skilled in the engineering and electrical arts that the present invention could find application wherever the moisture content of a non-metallic and particularly an organic material was required.

For simplicity the present invention will be described in respect of its use in the moisture sensing for timber. The particular use of the present invention is in association with a timber drying kiln.

BACKGROUND

A measurement of the moisture content of a non-metallic material may be required as part of a processing line. A ready example of a process requiring moisture measurement is the drying of timber in a kiln. If a measure of the moisture content of the timber is available, this can be used to control the drying time. This may result in in reduced electricity costs, which are becoming an increasingly large and volatile cost of production. Also, or alternatively, the product quality may be increased, through a reduction in the amount of under-dried product.

Various proposals have been put forward in the past in respect of moisture sensing using microwave technologies and including that invented by Wayne S Holmes, Stephen G Riley and Richard B Keam, the subject of international application PCT/NZ96/00134, published as International Publication Number WO 97/21992. Such earlier technology, whether using microwaves, capacitive or impedance systems all measured average moisture content of the timber. If the moisture content variation across the stack is to be determined, then to the present time this has required the use of sample boards, which are provided in the stack with moisture sensing probes inserted into them.

It is therefore an object of the present invention to provide an apparatus and method for moisture sensing using microwave technologies and which in the case of stacked timber will enable the moisture content of individual boards in the stack and the variation of moisture content across the stack to be determined.

Any discussion of the prior art throughout the specification should in no way be considered as an admission that such prior art is widely known or forms part of common general knowledge in the field.

SUMMARY OF THE INVENTION

According to one aspect of the present invention there is provided apparatus for sensing the permittivity of a material, the apparatus including a waveguide having a linear array of slots, a generator to generate one or more microwave signals and direct the microwave signals to the waveguide, measuring means to determine a scattering parameter or equivalent for either transmission direction of the waveguide in response to said one or more microwave signals, wherein in use the scattering parameter or equivalent indicates the permittivity of the material and the apparatus computes an indication of the permittivity of the material by averaging measurements obtained in both transmission directions of the waveguide.

Preferably, the generator may generate multiple frequencies and the apparatus may include a processing means adapted to, through the provision of an associated instruction set in a suitable storage medium, average measurements taken over the multiple frequencies.

Preferably, the waveguide may include n slots and the processing means may in use compute a measure of the permittivity, P, for each transmission direction using the equation:

$$P = a_0 + \sum_{j=1}^{15} (a_{1,j}S(f_j) + a_{2,j}S(f_j) + \ldots + a_{n-1,j}S(f_j) + a_{n,j}S(f_j))$$

wherein $S(f_j)$ is a scattering parameter measured in one direction for each of a plurality of frequencies j, $a_{i,j}$ (i=1, 2, . . . , n) are predetermined regression coefficients, determined for the respective transmission direction, and $a_0$ is one of either a further predetermined regression coefficient or a fixed value and wherein a total measure of permittivity is computed by averaging a computed measure of perimitivity for each transmission direction.

In an alternative embodiment, the waveguide may include n slots and the processing means may in use compute a measure of the permittivity, P1, using the equation:

$$P1 = a1_0 + \sum_{j=1}^{15} (a1_{1,j}S1(f_j) + a1_{2,j}S1(f_j) + \ldots + a1_{n-1,j}S1(f_j) + a1_{n,j}S1(f_j))$$

wherein $S1(f_j)$ is the average of the scattering parameter measured in both directions for each of a plurality of frequencies j, $a1_{i,j}$ (i=1, 2, . . . , n) are predetermined regression coefficients and $a1_0$ is one of either a further predetermined regression coefficient or a fixed value.

Preferably, the processing means may in use compute a measure of the permittivity, $P_i$, which is indicative of the permittivity at a slot i, using the equation:

$$P_i = a_0 + \sum_{j=1}^{m} a_{i,j}S(f_j)$$

Preferably, the apparatus may include a calibration function to determined the predetermined regression coefficients, wherein the calibration function includes measure the scattering parameter for a material of a known permittivity for each of a plurality of frequencies and using regression analysis to compute the regression coefficients.

Preferably, the apparatus may determine a first and a second set of regression coefficients for use in a first and a second transmission direction According to another aspect of the present invention there is provided a method for sensing the permittivity of a material, the method including providing a waveguide having a linear array of slots, transmitting one or more microwave signals through said waveguide and measuring a scattering parameter or equivalent for either transmission direction of the waveguide in response to said one or more microwave signals, wherein in use the scattering parameter or equivalent indicates the permittivity of the material and wherein the method includes computing an indication of the permittivity of the material by averaging measurements obtained in both transmission directions of the waveguide.

According to a further aspect of the present invention a method for sensing the moisture content of a material includes providing a waveguide having a linear array of slots, generating one or more microwave signals within said waveguide and measuring for either transmission direction through said waveguide, a scattering parameter and determining permittivity information provided in the scattering parameter the moisture content of the sample or portion of the material at a respective slot.

According to another aspect of the present invention there is provided apparatus for sensing the permittivity of a material, the apparatus including a waveguide having i slots arranged in a linear array, a generator to generate one or more microwave signals and direct the microwave signals to the waveguide, measuring means to determine a scattering parameter or equivalent for at least one transmission direction of the waveguide in response to said one or more microwave signals, wherein in use the scattering parameter or equivalent indicates the permittivity of the material, and wherein the permittivity of the material substantially at a measurement slot is computed by multiplying the scattering parameter or equivalent by a regression coefficient corresponding to said measurement slot, the regression coefficient being one of i regression coefficients determined by regression analysis during a calibration process.

According to another aspect of the present invention there is provided apparatus for sensing the permittivity of a material, the apparatus including a waveguide having i slots arranged in a linear array, a generator to generate one or more microwave signals and direct the microwave signals to the waveguide, measuring means to determine a scattering parameter or equivalent for at least one transmission direction of the waveguide in response to said one or more microwave signals, wherein a value $P_i$ indicative of the permittivity of the material at a slot i, is computed using the equation:

$$P_i = a_0 + \sum_{j=1}^{m} a_{i,j} S(f_j)$$

wherein $S(f_j)$ is a scattering parameter or equivalent measured in one direction for each of a plurality of frequencies j;

m is the number of said one or more frequencies;

$a_{i,j}$ (i=1, 2, . . . , n) are predetermined regression coefficients, determined for the respective transmission direction by regression analysis of the equation:

$$P = a_0 + a_{1,j} S(f_j) + a_{2,j} S(f_j) + \ldots + a_{n-1,j} S(f_j) + a_{n,j} S(f_j)$$

with a set of values known for P and $S(f_j)$; and $a_0$ is one of either a further predetermined regression coefficient or a fixed value.

Preferably, the measuring means may in use determine a scattering parameter or equivalent for both transmission directions of the waveguide, wherein a total measure of permittivity is computed by the processing means by computing an average of a measure of permittivity for each transmission direction.

Preferably, the apparatus may determine a first and a second set of regression coefficients for use in a first and a second transmission direction.

Preferably, the measure of permittivity may be used to indicate the moisture content of the material.

According to another aspect of the present invention, there is provided a method of controlling a drier, the method including providing apparatus for sensing the permittivity of a material as described herein above, using said apparatus for obtaining measurements of the permittivity and thus the moisture content of a material being dried substantially at two or more slots and adjusting the drying time to minimise the measured moisture at a first slot while keeping the measured moisture at a second slot above a minimum level.

Preferably, the method may include controlling one or more fans and or heating elements to modify the drying conditions in the drier in response to variation of measured moisture between slots.

According to another aspect of the present invention, there is provided a method of controlling a drier, the method including providing apparatus for sensing the permittivity of a material as described herein above, using said apparatus for obtaining measurements of the permittivity and thus the moisture content of a material being dried substantially at two or more slots and adjusting one or more fans and or heating elements to modify the drying conditions in the drier in response to variation of measured moisture between slots.

According to a still further aspect of the present invention an apparatus and/or method for moisture sensing using microwave technologies is substantially as herein described.

Further aspects of this invention which should be considered in all its novel aspects should become apparent from the following description given by way of example and with reference to preferred embodiments thereof and in which reference is made to the accompanying drawings.

MODES FOR CARRYING OUT THE INVENTION

Microwave and other technologies have been used in the past to determine the average moisture content of a stack of timber or other material.

The present invention however, has been developed to enable the moisture content of individual samples in a stack of boards to be measured as well as the average moisture content, this being of particular benefit in determining the variability of moisture content across the stack. In achieving this, the present invention has utilised the scanning of a range of frequencies and determines the moisture content of material at each individual slot in a waveguide having a linear array of slots. Also, improved accuracy may be obtained for measurement of the average moisture content.

Although the description provided herein has been given by way of example of preferred embodiments with particular reference to an application of the invention to measurement of moisture across a stack of timber boards, the present invention may have alternative applications to a range of materials. Furthermore, although the invention is expected to have particular application to the detection of moisture content, the invention may detect any characteristic that results in a change in the permittivity of the material.

Figure 1:
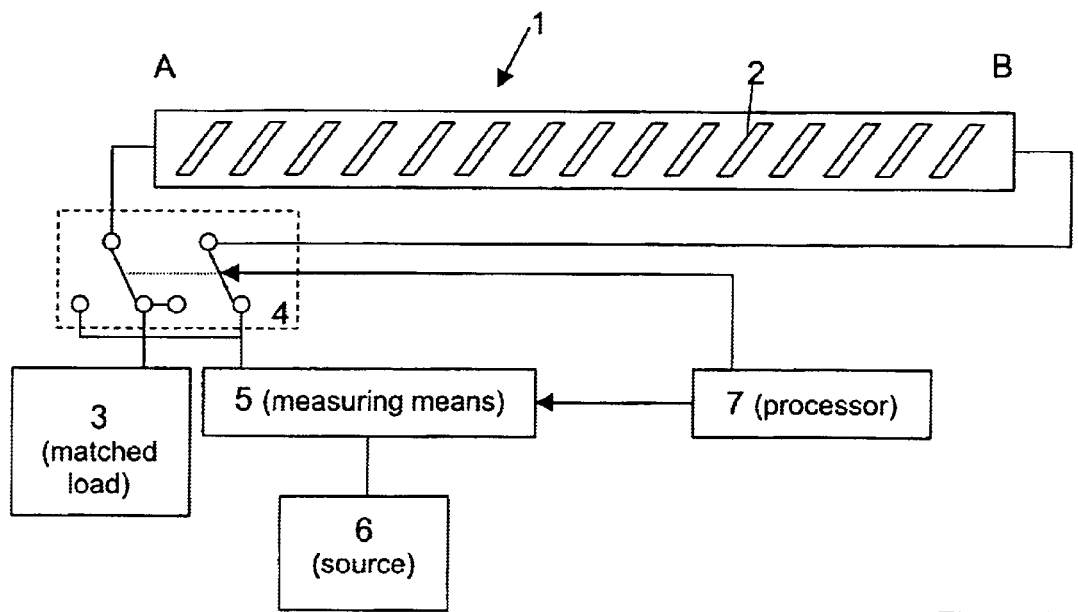
FIG. 1: shows very diagrammatically a moisture content measuring apparatus according to one possible embodiment to the invention.

Referring to FIG. 1 a waveguide referenced generally by arrow 1 is shown with a linear array of slots 2 provided in a wall, the slots angled at a suitable angle relative to the longitudinal axis of the waveguide. The slots, by way of example, may be at an angle of 52° relative to the longitudinal axis of the waveguide 1 and separated by a distance of 50 mm for a frequency range of 7.0 GHz to 7.7 GHz. However, for other frequency ranges, the slot angle and separation may be chosen so that at the mid point in the frequency range, the slots themselves offer minimal reflections in air. This arrangement may maximise the response to the covering timber.

The waveguide 1 has ports A and B at respective ends, which ports are able to be selectively terminated in a matched load 3, which is matched to the impedance of the waveguide 1, while a measurement of reflectance is made at the other end.

Measurements of the microwave scattering parameters at discrete frequency points over a suitable frequency span, suitably of the order of 1 GHz, are taken. A microwave sixport reflectometer 5 may be used to obtain the measurements. Any other suitable means to measure reflectance may be used as will be apparent to those skilled in the relevant arts, such as a vector network analyser. However, a sixport reflectometer may be preferred, due to cost, size, portability and simplicity of use considerations.

Figure 2:
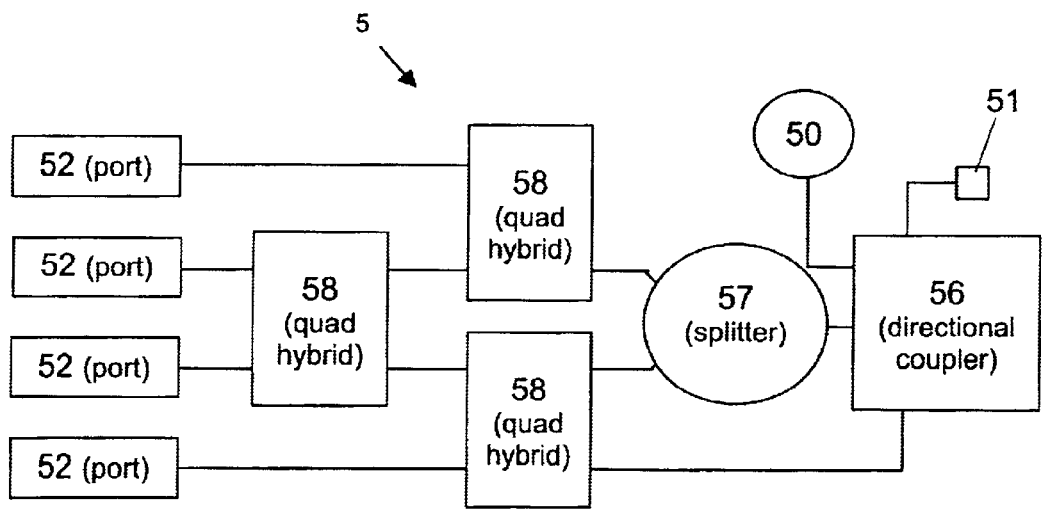
FIG. 2: shows a block diagram of the sixport reflectometer shown in FIG. 1.

A block diagram of a sixport reflectometer 5 suitable for use for the purposes of the present invention is shown in FIG. 2. The sixport reflectometer 5 receives the microwave signals from a microwave source 6 at port 50, transmits and receives microwave signals to and from the waveguide 1 at port 51 and the four measurement ports 52 to 55 provide voltage signals to a computer, which may be a signal processor 7. The signal processor 7 then evaluates the magnitude and phase of the reflections.

The sixport reflectometer 5 includes a directional coupler 56, a splitter 57 and three quad hybrids 58 to simulate a transmission line within the sixport reflectometer 5.

The signal processor 7 may be any suitable processor for computing the scattering parameters (s-parameters) $S_{aa}$ and $S_{bb}$ or other value indicative of reflectance.

The signal processor 7 also controls the operation of the switch 4 to control the obtaining of measurements from both ports.

A suitable microwave source 6 for the purposes of the present invention, for example, is a YIG oscillator. A YIG oscillator provides sufficient power (10–100 mW typically) to drive the sixport reflectometer 5. A low pass filter may be used to reduce the presence of second harmonic in the signal as required. Attenuation of the second harmonic to 25 dB down from the fundamental frequency has been found sufficient for the purposes of the invention, although more or less attenuation may be used depending on the specific requirements for the system as may be readily determined by those skilled in the art.

The microwave signals generated by the microwave source 6 are communicated through a waveguide to the sixport reflectometer 5. As referred to above, the sixport reflectometer 5 allows measurements to be taken of both the magnitude and phase of the received reflected microwave energy, which varies depending on the permittivity of the material placed adjacent the slots, thereby allowing calculation of the scattering parameters (s-parameters) by the signal processor 7. In this way the s-parameters are determined at multiple frequencies and in both directions. The s-parameters $S_{aa}$, $S_{bb}$, may be used for calculation of the moisture content.

The microwave s-parameters $S_{aa}$, $S_{bb}$ contain information related to the permittivity of the individual samples, each sample corresponding to a slot and this in turn depends upon the moisture content of the individual samples. Thus, the total moisture content ($W_{TOT}$, in weight percent) over the stack of timber measured in one direction can then be obtained according to equation 1.

$$W_{TOT} = a_0 + \sum_{j=1}^{15} (a_{1,j}S(f_j) + a_{2,j}S(f_j) + \ldots + a_{14,j}S(f_j) + a_{15,j}S(f_j)) \quad \text{equation 1}$$

Where:
$a_0$ is a constant.
$a_{i,j}$ (i=1, 2 ..., 15) are predetermined regression coefficients for slot i (see herein below).
i represents the slot number/sample number from the port of the waveguide (port A or port B).
$S(f_j)$ are the measured amplitudes of the average of the s-parameters $S_{aa}$ or $S_{bb}$ over the frequency range $f_j$ ($f_j$=6.95+j*0.05 GHz for j=1, 2, ..., 14, 15).

The s-parameter measurement $S(f_j)$ in equation 1 may be determined by summing, averaging or otherwise combining the measured values of $S_{aa}$ or $S_{bb}$ for each frequency to obtain a single value representative of the measurements obtained over the frequency range. Alternatively, $W_{TOT}$ may be calculated for each frequency and averaged to obtain the final moisture measurement.

In a further alternative embodiment a combination of s-parameter terms may be used for each slot, for example $S(f_j)$ may equal the sum of $S_{aa}$ and $S_{ab}$ or some other combination of s-parameter terms, reflection coefficients or similar. Thus, $S(f_j)$ may take many different forms. One example of such a form is given in equation 1A.

$$W_{TOT} = a_0 + \sum_{j=1}^{15} (a_{1,j}S2(f_j) + a_{2,j}S2(f_j) + \ldots + a_{14,j}S2(f_j) + a_{15,j}S2(f_j)) \quad \text{equation 1A}$$

Where $S2(f_j)=S_{aa}+S_{ab}$ for measurement in one direction and $S_{bb}+S_{ba}$ for measurement in the other direction.

The measurement is repeated for the opposite direction to obtain a measurement of the s-parameter ($S_{bb}$ or $S_{aa}$) for the other port and the value or values of W averaged across the two measurements. Measurement for the other port is obtained by switching switch 4. The bi-directional measurement and the use of multiple frequencies $f_j$ each assist in increasing the accuracy and reliability of the measurements. Thus, while the invention may be implemented taking one measurement of S(f) at a single frequency, it is expected that much improved accuracy may be obtained by using multiple frequencies in both directions and averaging the results.

The $a_{i,j}$ terms describe the interactions between the slots and are determined prior to the calculation of $W_{TOT}$ through a calibration process, which includes taking a measurement of one or more calibration materials whose permittivity is known. The use of more than two calibration materials is expected to increase accuracy. The same number of $a_{i,j}$ terms, (excluding $a_0$) is used as there are slots in the waveguide 1. So, a waveguide with 15 slots has 15 $a_{i,j}$ terms, $a_{1,j}$ to $a_{15,j}$ plus $a_0$. The $a_0$ term may be determined as part of the regression analysis, which is the preferred form of the invention, or alternatively may be set to a predetermined value, such as zero. If a waveguide having more slots is used, the number of regression coefficients is correspondingly increased. The step size between frequency measurements may be varied depending on the number of regression coefficients required.

To calibrate the system, wood of known moisture content may be placed over the slots, but any other material having similar permittivity could be used. Measurements of the scattering parameters $S_{aa}$ and $S_{bb}$ are taken for each frequency. This leads to an overdetermined system relating W to S(f). The $a_{i,j}$ terms in equation 1 may thus be calculated using regression analysis. As the moisture content of the calibration material is known and the scattering parameter terms can be measured, the only unknown variables in equation 1 are the $a_{i,j}$ terms. Using a suitable error minimisation algorithm or similar regression analysis tool, the $a_{i,j}$ terms may be determined. To increase accuracy, the $a_{i,j}$ terms are computed for each direction (i.e. one using $S_{aa}$ and the other using $S_{bb}$), resulting in two sets of $a_{i,j}$ terms.

The regression coefficients corresponding to individual slots may in one embodiment be obtained from a set of over 417 measurements of $S(f_j)$ corresponding to 15 frequencies. Any number of frequencies may be used, with a minimum number corresponding to the number of slots.

The moisture content for individual samples, wherein each sample corresponds to a slot, can be obtained directly. A value indicative of moisture content $W_i$ for each sample is obtained using equation 2.

$$W_i = a_0 + \sum_{j=1}^{15} a_{i,j} S(f_j) \qquad \text{equation 2}$$

By way of example, the coefficient $a_{1,j}$ (which was calculated during the calibration process), is used in equation 2 with the measured values of the scattering parameters $S(f_j)$ (which is the average of the measured $S_{aa}$ and $S_{bb}$), over the frequency range to calculate the reflectance at slot 1.

Those skilled in the relevant arts will appreciate that the microwave signals transmitted to and received from the waveguide 1 may be mathematically treated according to a number of different methodologies. For example, although the description herein has been given with particular reference to a system based on the standard notation of scattering parameters, the reflection coefficient at the ports $\Gamma_a$ and $\Gamma_b$ may equivalently be used or the s-parameters $S_{aa}$ and $S_{bb}$ used with appropriate scaling of the "a" terms in equations 1 and 2. Furthermore, the values of the scattering parameters or reflection coefficients may be transformed if required for the particular analysis or signal processing requirements.

Figure 3:
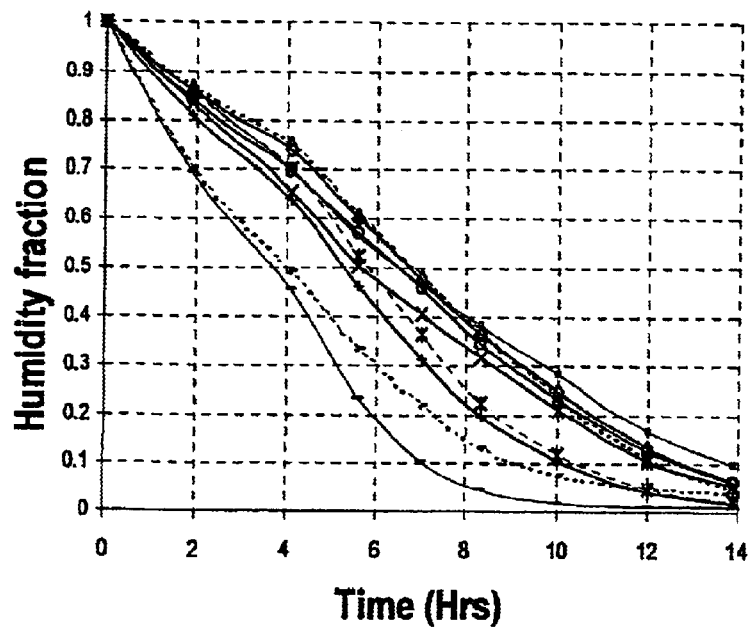
FIG. 3: shows a drying profile for drying timber boards stacked in a kiln.

The drying time and the rate of drying over time for timber varies depending on the initial moisture content of the timber. This is shown in FIG. 3, which is a normalised plot of humidity content of wood over time for a number of different timber stacks having a different initial humidity. To accommodate for variability in the drying process, the system is calibrated each time a timber stack having a largely different initial moisture content is to be measured.

In practice however, the moisture content of the timber is known before drying commences. Therefore, a number of calibrations may be performed and the most appropriate one chosen for a particular stack of timber to be measured depending on which has the closest initial moisture content to the incoming timber. This prevents having to perform a calibration each time a new source of timber is used.

Once measurements have been obtained of the moisture content across the entire stack using equation 1 and for each sample/slot using equation 2, this information can be used to control the drying process. An operator may vary the length of the drying time to dry the sample with the highest moisture content as much as possible before the driest sample reaches a critical level. For example, if the goal moisture content is 10%, drying may continue until the driest sample reaches a minimum level such as 2%. This may allow the highest moisture samples to be dried to a value closer to 10%.

In addition, the operator may change the conditions within the kiln dependent on the moisture profile across the stack. If the individual sample measurements indicate increased moisture at one end, the operator may operate fans, turn heating elements on or off or similar to make the moisture content across the stack more even.

Thus, the present invention may be used to provide increased information on the drying of a stack of timber, permitting increased control over the drying process and increased consistency in drying.

Where in the foregoing description, reference has been made to specific components or integers of the invention having known equivalents then such equivalents are herein incorporated as if individually set forth.

Although this invention has been described by way of example and with reference to possible embodiments thereof, it is to be understood that modifications or improvements may be made thereto without departing from the scope of the invention as defined in the appended claims.

What is claimed is:

1. Apparatus for sensing the permittivity of a material, the apparatus comprising a waveguide having a linear array of slots, a generator to generate one or more microwave signals and direct the microwave signals to the waveguide, measuring means to determine a scattering parameter or equivalent for either transmission direction of the waveguide in response to said one or more microwave signals, wherein in use the scattering parameter or equivalent indicates the permittivity of the material and the apparatus computes an indication of the permittivity of the material by averaging measurements obtained in both transmission directions of the waveguide.

2. The apparatus of claim 1, wherein the generator generates multiple frequencies and the apparatus further comprises a processing means adapted to, through the provision of an associated instruction set in a suitable storage medium, average measurements taken over the multiple frequencies.

3. The apparatus of claim 2, wherein the waveguide comprises n slots and the processing means in use computes a measure of the permittivity, P, for each transmission direction using the equation:

$$P = a_0 + \sum_{1}^{j} (a_{1,j}S(f_j) + a_{2,j}S(f_j) + \ldots + a_{n-1,j}S(f_j) + a_{n,j}S(f_j))$$

wherein $S(f_j)$ is a scattering parameter measured in one direction for each of a plurality of frequencies j, $a_{i,j}$ (i=1, 2, . . . , n) are predetermined regression coefficients, determined for the respective transmission direction, and $a_0$ is one of either a further predetermined regression coefficient or a fixed value and wherein a total measure of permittivity is computed by averaging a computed measure of permittivity for each transmission direction.

4. The apparatus of claim 3, further comprising a calibration function to determine the predetermined regression coefficients, wherein the calibration function comprises measuring the scattering parameter for a material of a known permittivity for each of a plurality of frequencies and using regression analysis to compute the regression coefficients.

5. The apparatus of claim 4, wherein the apparatus determines a first and a second set of regression coefficients for use in a first and a second transmission direction respectively.

6. The apparatus of claim 2, wherein the waveguide comprises n slots and the processing means in use computes a measure of the permittivity, P1, using the equation:

$$P1 = a1_0 + \sum_{1}^{j} (a1_{1,j}S1(f_j) + a1_{2,j}S1(f_j) + \ldots + a1_{n-1,j}S1(f_j) + a1_{n,j}S1(f_j))$$

wherein $S1(f_j)$ is the average of the scattering parameter measured in both directions for each of a plurality of frequencies j, $a1_{i,j}$ (i=1, 2, . . . , n) are predetermined regression coefficients and $a1_0$ is one of either a further predetermined regression coefficient or a fixed value.

7. The apparatus of claim 6, further comprising a calibration function to determine the predetermined regression coefficients, wherein the calibration function comprises measuring the scattering parameter for a material of a known permittivity for each of a plurality of frequencies and using regression analysis to compute the regression coefficients.

8. The apparatus of claim 7, wherein the apparatus determines a first and a second set of regression coefficients for use in a first and a second transmission direction respectively.

9. The apparatus of claim 2, wherein the waveguide comprises n slots and wherein the processing means in use computes a measure of the permittivity, $P_i$, which is indicative of the permittivity at a slot i, using the equation:

$$P_i = a_0 + \sum_{1}^{j} a_{i,j}S(f_j)$$

wherein $S(f_j)$ is an average of a scattering parameter measured in one or both directions for each of a plurality of frequencies j, $a_{i,j}$ are predetermined regression coefficients and $a_0$ is one of either a further predetermined regression coefficient or a fixed value.

10. The apparatus of claim 1, wherein the measure of permittivity is used to indicate the moisture content of the material.

11. A method of controlling a drier, the method comprising
providing apparatus for sensing the permittivity of a material as claimed in claim 1, using said apparatus for obtaining measurements of the permittivity and thus the moisture content of a material being dried substantially at two or more slots and adjusting the drying time to minimise the measured moisture at a first slot while keeping the measured moisture at a second slot above a minimum level.

12. The method of claim 11, comprising controlling one or more fans and or heating elements to modify the drying conditions in the drier in response to variation of measured moisture between slots.

13. A method of controlling a drier, the method comprising
providing apparatus for sensing the permittivity of a material as claimed in claim 1,
using said apparatus for obtaining measurements of the permittivity and thus the moisture content of a material being dried substantially at two or more slots, and adjusting one or more fans and or heating elements to modify the drying conditions in the drier in response to variation of measured moisture between slots.

14. A method for sensing the permittivity of a material, the method comprising
providing a waveguide having a linear array of slots,
transmitting one or more microwave signals through said waveguide and measuring a scattering parameter or equivalent for either transmission direction of the waveguide in response to said one or more microwave signals,
wherein in use the scattering parameter or equivalent indicates the permittivity of the material and wherein the method comprises computing an indication of the permittivity of the material by averaging measurements obtained in both transmission directions of the waveguide.

15. A method for sensing the moisture content of a sample comprising
locating a waveguide having a linear array of slots next to the sample,
generating one or more microwave signals within said waveguide and measuring for either transmission direction through said waveguide, a scattering parameter, and
determining from permittivity information provided by the scattering parameter the moisture content of the sample or portion of the sample at a respective slot.

16. The method of claim 15, wherein the waveguide comprises n slots and wherein the step of determining the permittivity information, $P_i$, at a slot i, comprises using the equation:

$$P_i = a_0 + \sum_{1}^{j} a_{i,j}S(f_j)$$

wherein $S(f_j)$ is an average of a scattering parameter measured in one or both directions for each of a plurality of frequencies j $a_{i,j}$ are predetermined regression coefficients and $a_0$ is one of either a further predetermined regression coefficient or a fixed value.

17. Apparatus for sensing the permittivity of a material, the apparatus comprising
a waveguide having n slots arranged in a linear array,
a generator to generate one or more microwave signals and direct the microwave signals to the waveguide, measuring means to determine a scattering parameter or equivalent for at least one transmission direction of the waveguide in response to said one or more microwave signals, wherein in use the scattering parameter or equivalent indicates the permittivity of the material, and wherein the permittivity of the material substantially at a measurement slot is computed by multiplying the scattering parameter or equivalent by a regression coefficient corresponding to said measurement slot, the regression coefficient being one of n regression coefficients determined by regression analysis during a calibration process.

18. The apparatus of claim 17, wherein the measure of permittivity is used to indicate the moisture content of the material.

19. A method of controlling a drier, the method comprising providing apparatus for sensing the permittivity of a material as claimed in claim 17, using said apparatus for obtaining measurements of the permittivity and thus the moisture content of a material being dried substantially at two or more slots, and adjusting the drying time to minimise the measured moisture at a first slot while keeping the measured moisture at a second slot above a minimum level.

20. The method of claim 19, further comprising controlling one or more fans and or heating elements to modify the drying conditions in the drier in response to variation of measured moisture between slots.

21. A method of controlling a drier, the method comprising providing apparatus for sensing the permittivity of a material as claimed in claim 17, using said apparatus for obtaining measurements of the permittivity and thus the moisture content of a material being dried substantially at two or more slots, and adjusting one or more fans and or heating elements to modify the drying conditions in the drier in response to variation of measured moisture between slots.

22. Apparatus for sensing the permittivity of a material, the apparatus comprising a waveguide having n slots arranged in a linear array, a generator to generate one or more microwave signals and direct the microwave signals to the waveguide, measuring means to determine a scattering parameter or equivalent for at least one transmission direction of the waveguide in response to said one or more microwave signals, wherein a value $P_i$ indicative of the permittivity of the material at a slot i, is computed using the equation:

$$P_i = a_0 + \sum_{j=1}^{m} a_{i,j} S(f_j)$$

wherein $S(f_j)$ is a scattering parameter or equivalent measured in one direction for each of a plurality of frequencies j;

m is the number of said one or more frequencies;

$a_{i,j}$ (i=1, 2, . . . , n) are predetermined regression coefficients, determined for the respective transmission direction by regression analysis of the equation:

$$P = a_0 + \sum_{1}^{j} (a_{1,j} S(f_j) + a_{2,j} S(f_j) + \ldots + a_{n-1,j} S(f_j) + a_{n,j} S(f_j))$$

with a set of values known for P and $S(f_j)$;

and $a_0$ is one of either a further predetermined regression coefficient or a fixed value.

23. The apparatus of claim 22, further comprising processing means, wherein the measuring means in use determines a scattering parameter or equivalent for both transmission directions of the waveguide, wherein a total measure of permittivity is computed by the processing means by computing an average of a measure of permittivity for each transmission direction.

24. The apparatus of claim 23, wherein the apparatus determines a first and a second set of regression coefficients for use in a first and a second transmission direction.

* * * * *